United States Patent
Hwang et al.

(10) Patent No.: US 11,543,357 B2
(45) Date of Patent: Jan. 3, 2023

(54) METAL SORTING SYSTEM USING LASER INDUCED BREAKDOWN SPECTROSCOPY AND OPERATING METHOD THEREOF

(71) Applicant: Gwangju Institute of Science and Technology, Gwangju (KR)

(72) Inventors: Eui Seok Hwang, Gwangju (KR); E Den Kim, Gwangju (KR); Sung Ho Jeong, Gwangju (KR); Sung Ho Shin, Gwangju (KR)

(73) Assignee: Gwangju Institute of Science and Technology, Gwangju (KR)

( * ) Notice: Subject to any disclaimer, the term of this patent is extended or adjusted under 35 U.S.C. 154(b) by 730 days.

(21) Appl. No.: 16/534,824

(22) Filed: Aug. 7, 2019

(65) Prior Publication Data

US 2020/0049628 A1 Feb. 13, 2020

(30) Foreign Application Priority Data

Aug. 8, 2018 (KR) .......................... 10-2018-0092251

(51) Int. Cl.
*G01N 21/71* (2006.01)
*G01N 33/2028* (2019.01)

(52) U.S. Cl.
CPC ....... *G01N 21/718* (2013.01); *G01N 33/2028* (2019.01)

(58) Field of Classification Search
CPC .......................... G01N 21/718; G01N 33/2028
See application file for complete search history.

(56) References Cited

U.S. PATENT DOCUMENTS

2014/0268133 A1\* 9/2014 McManus ................ G01J 3/28
356/316

FOREIGN PATENT DOCUMENTS

| KR | 20090094559 A | 9/2009 |
| KR | 20120063166 A | 6/2012 |
| WO | WO2008122622 A1 | 10/2008 |

\* cited by examiner

*Primary Examiner* — Jamil Ahmed

(57) ABSTRACT

Disclosed is an operating method of a metal sorting system using laser induced breakdown spectroscopy (LIBS), which may include: analyzing a metal component distribution for various metals using LIBS library information; setting multiple clusters according to the metal component distribution; performing first regression component analysis with respect to spectral data of a metal sample; calculating a probability that the spectral data will belong to each of the set multiple clusters using the first regress component analysis result; performing second regression component analysis with respect to the spectral data which belong to each cluster; and discriminating a type of metal sample by a weighted sum of the calculated probability and the second regression component analysis result.

13 Claims, 7 Drawing Sheets

[Fig. 1]
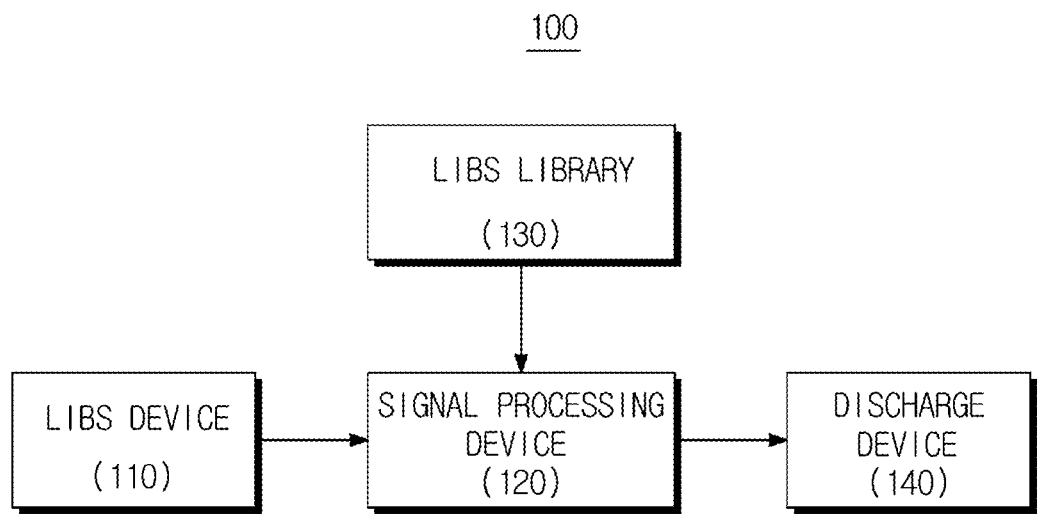

[Fig. 2]
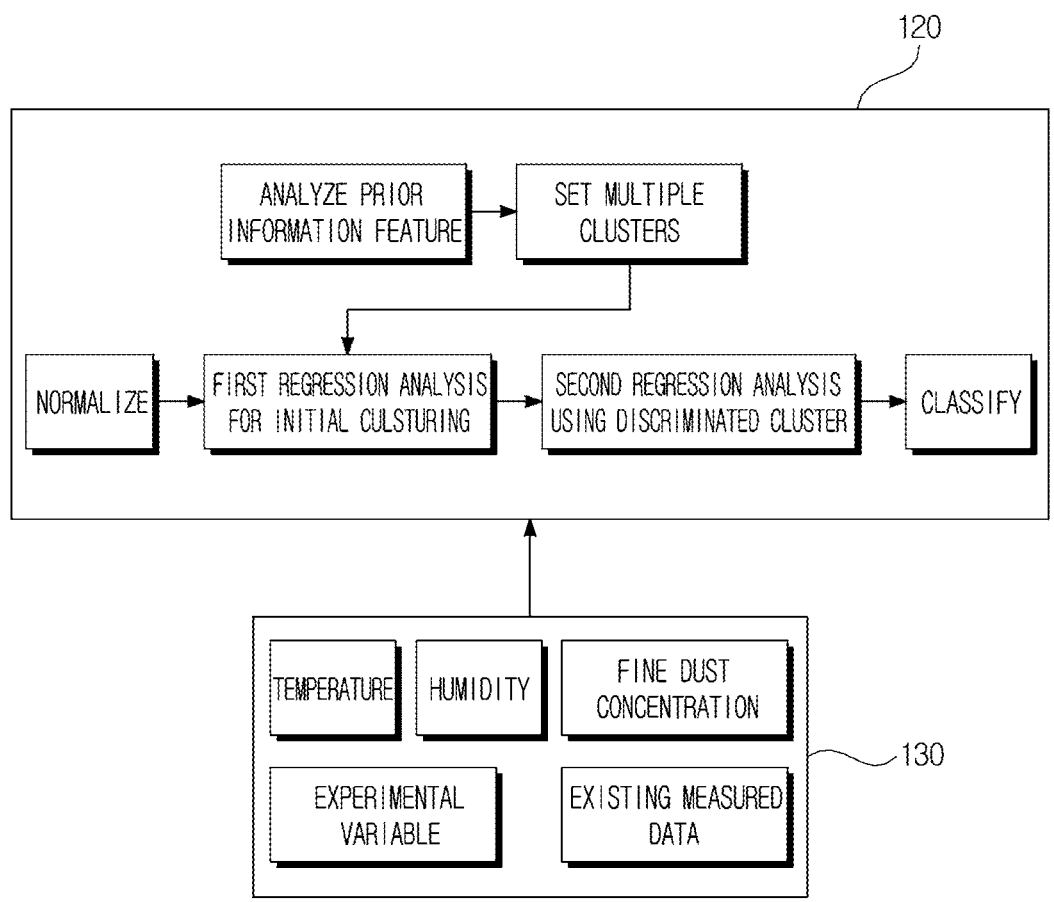

[Fig. 3]
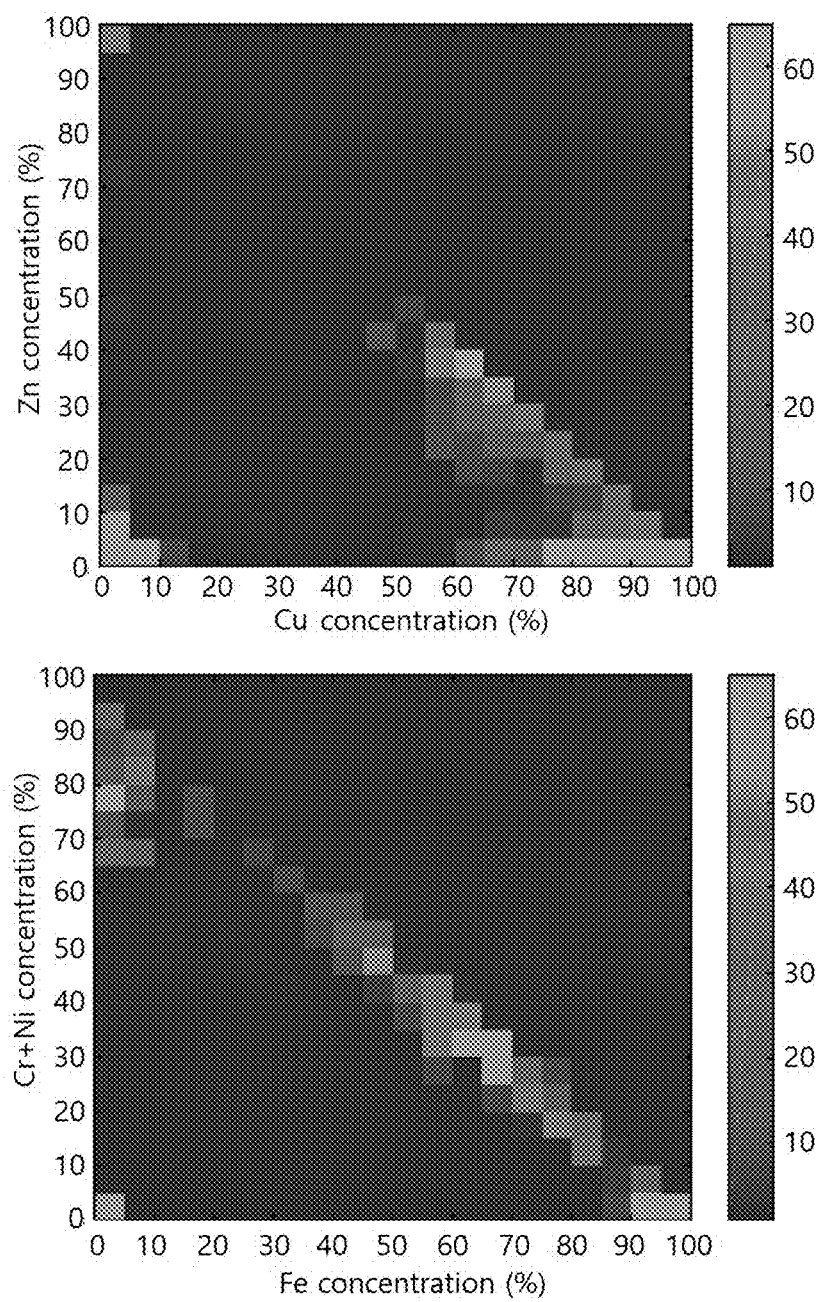

[Fig. 4]
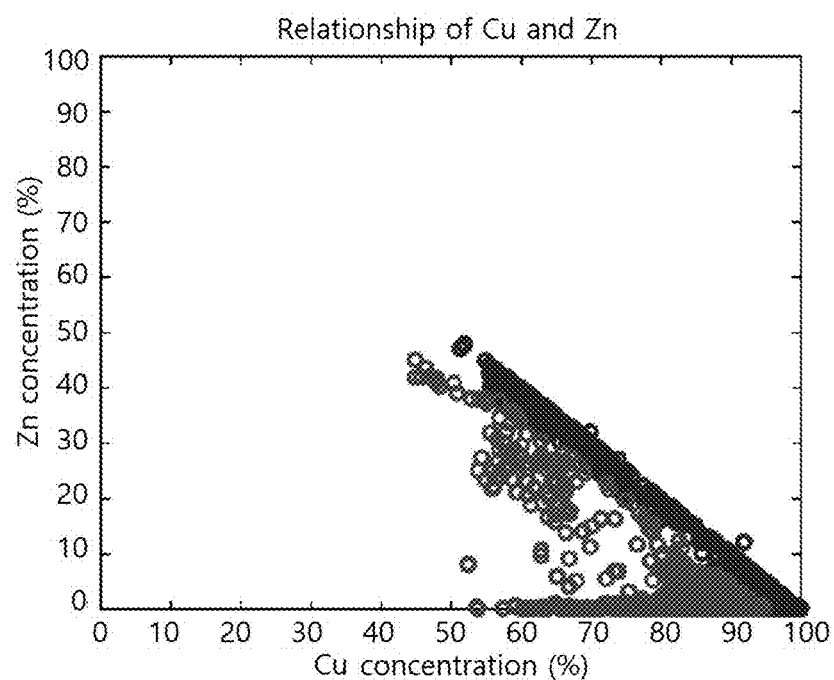
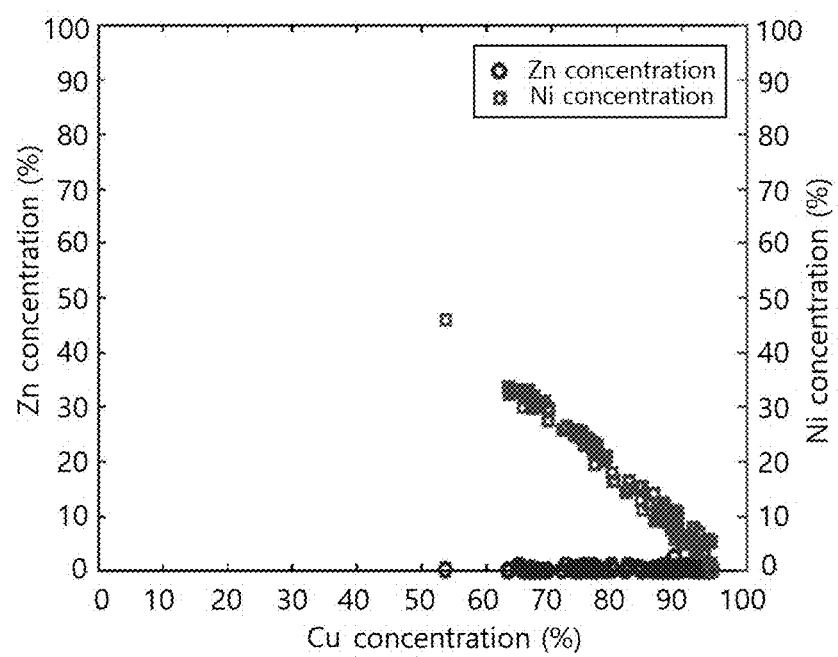

[Fig. 5]
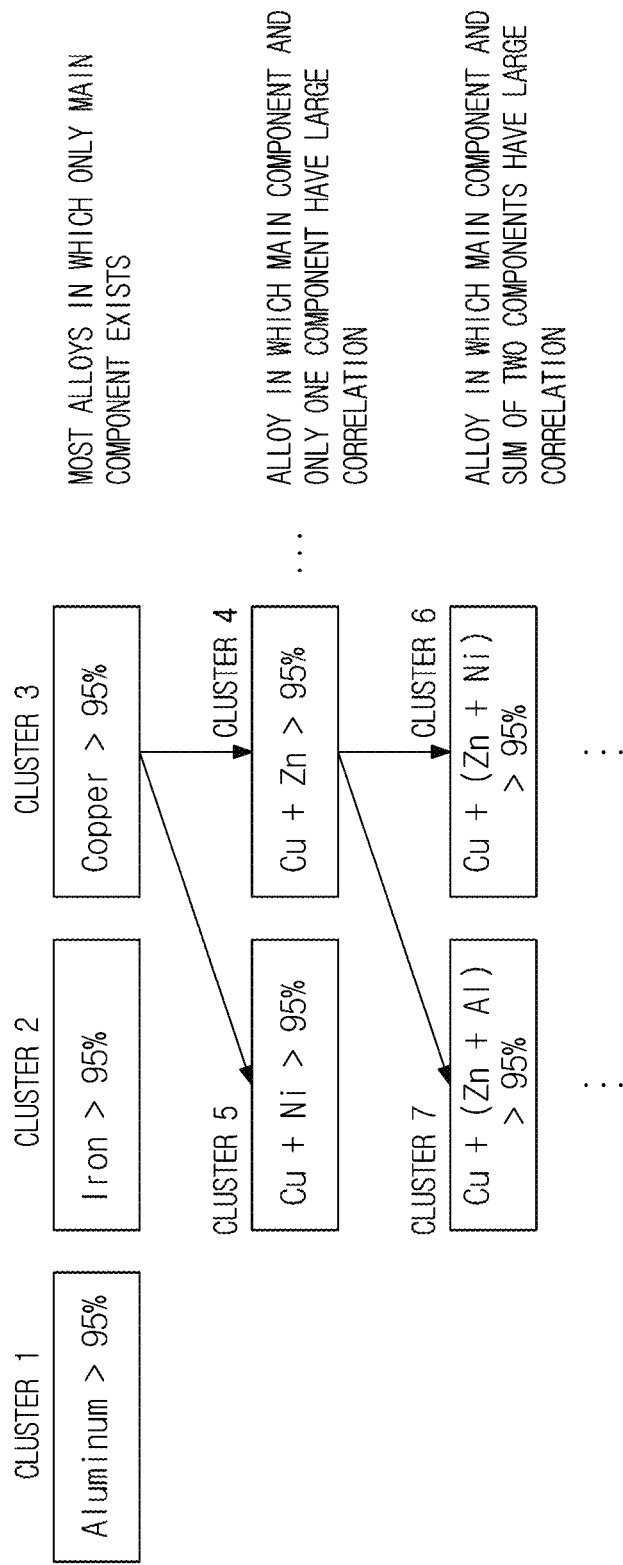

[Fig. 6]
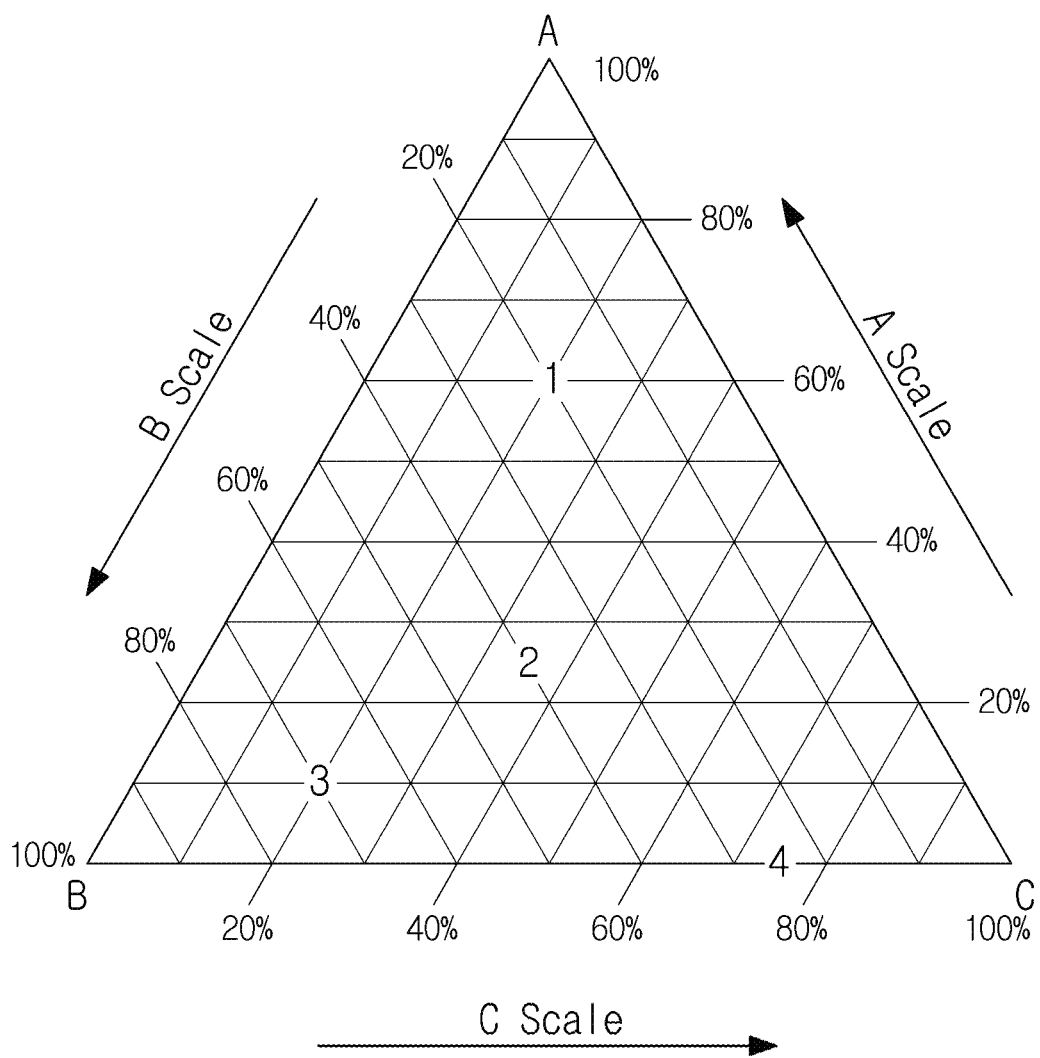

[Fig. 7]
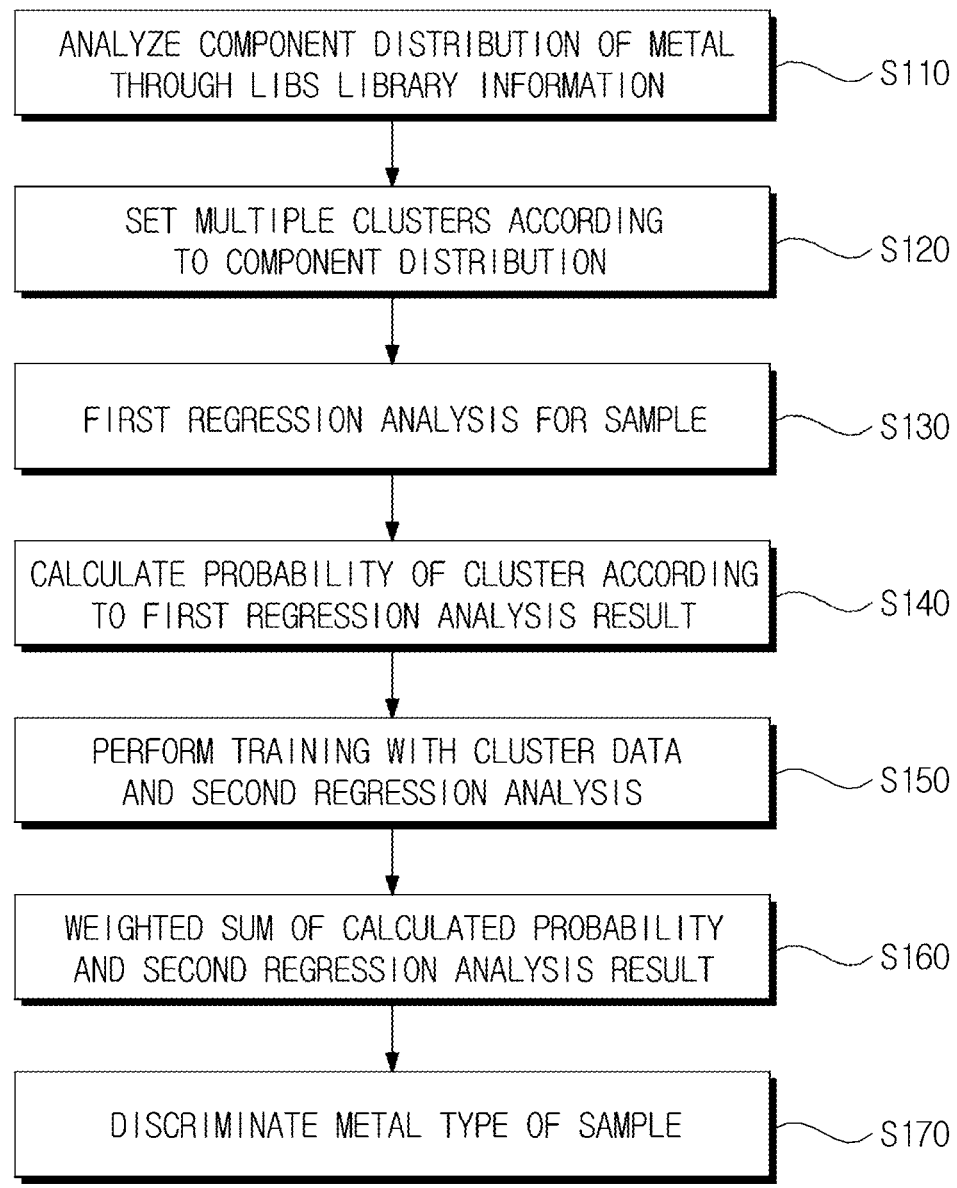

METAL SORTING SYSTEM USING LASER INDUCED BREAKDOWN SPECTROSCOPY AND OPERATING METHOD THEREOF

CROSS-REFERENCE TO RELATED APPLICATIONS

This application claims priority to and the benefit of Korean Patent Application No. 10-2018-0092251 filed in the Korean Intellectual Property Office on Aug. 8, 2018, the entire contents of which are incorporated herein by reference.

TECHNICAL FIELD

The present invention relates to a metal sorting system using laser induced breakdown spectroscopy (LIBS) and an operating method thereof.

BACKGROUND ART

Recently, recycling has been a national emphasis project on saving resources and has been being promoted not only in Korea hut also all over the world. Waste resource sorting technologies in the related art include plastic sorting using near-infrared rays, color sorting using visible light, and metal sorting using X-ray, but the usability is evaluated to be low. In the case of electromagnetic sensors, sorting of metals and nonmetals is possible, but sorting by metals is impossible. In order to replace the sorting, there is a growing global interest in a system that sorts automatically selected waste resources based on laser induced breakdown spectroscopy (LIBS) accurately and quickly in real time.

Most of the metal materials used in the real world have many complex materials composed of various components. In addition, when the distribution of each component is examined, a feature that the concentration is concentrated at a specific concentration rather than a constant distribution may be confirmed. Looking at the distribution characteristics of each of the components of the metals, there are metals that exhibit a multi-dimensional correlation with respect to certain components. From the viewpoint of metal sorting, metal sorting according to a multidimensional correlation can increase the accuracy because lines of other spectra correlated more than spectral lines of a main component have a greater influence.

Korean Patent Unexamined Publication No: 10-2012-0063166, Publication date: Jun. 15, 2012, Invention Title: Metal Scrap Sorting and Recovery System Korean Patent Unexamined Publication No. 10-2009-0094559, Publication date: Sep. 8, 2009, Invention Title: Device for Automatic Selection of Scrap International Unexamined Publication No. WO/2008/122622, Publication date: Oct. 16, 2008, Invention Title: DEVICE AND METHOD FOR ANALYZING A HETEROGENEOUS MATERIAL BY MEANS OF LASER-INDUCED PLASMA SPECTROSCOPY

SUMMARY OF THE INVENTION

The present invention has been made in an effort to provide a metal sorting system capable of sorting metal more precisely and an operating method thereof.

An exemplary embodiment of the present invention provides an operating method of a metal sorting system using laser induced breakdown spectroscopy (LIBS), which may include: analyzing a metal component distribution for various metals using LIBS library information; setting multiple clusters according to the metal component distribution; performing first regression component analysis using first training data with respect to spectral data of a metal sample; calculating a probability that the spectral data will belong to each of the set multiple clusters using the first regress component analysis result; performing second regression component analysis using second training data which belongs to each cluster with respect to the spectral data of the metal sample; and discriminating a type of metal sample by a weighted sum of the calculated probability and the second regression component analysis result.

In the exemplary embodiment, the LIBS library information may include prior information including at least one of a temperature, humidity, fine dust concentration, experimental variables, and existing measured data.

In the exemplary embodiment, the metal component distribution may include information on a correlation between the LIBS library information and the metal.

In the exemplary embodiment, the setting of the multiple clusters may include classifying the clusters by considering a main component, and classifying the clusters by considering a linear relationship between a component having a first concentration and the main component, and the first concentration may be lower than a concentration of the main component.

In the exemplary embodiment, the setting of the multiple clusters may further include classifying the clusters by considering the linear relationship between a component having the second concentration and the main component, and the second concentration may be lower than the first concentration.

In the exemplary embodiment, the calculating of the probability may further include performing soft sorting for the metal sample according to the calculated probability.

In the exemplary embodiment, the calculating of the probability may include calculating a probability that the spectral data will belong to each cluster using a Bayesian rule.

In the exemplary embodiment, the performing of the first regression component analysis may include estimating an element concentration of unknown metal data by training the spectral data using the first training data, and the first training data may be all training data.

In the exemplary embodiment, the performing of the second regression component analysis may include estimating the element concentration of the unknown metal data by training the spectral data using the second training data.

In the exemplary embodiment, the discriminating the type of metal sample may include calculating a final regression analysis result by the weighted sum of the second regression component analysis result and the calculated probability, estimating at least one metal concentration value depending on the final regression analysis result, and discriminating the type of metal sample using the LIBS library information and the estimated concentration value.

Another exemplary embodiment of the present invention provides a metal sorting system using laser induced breakdown spectroscopy (LIBS), which includes: an LIBS device outputting spectral data of a metal sample by irradiating the metal sample with a laser; a signal processing device discriminating a type of metal sample using the spectral data and LIBS library information; and a discharge device discharging metals to different collection boxes according to the discriminated metal type, in which the signal processing device sets multiple clusters according to a metal component distribution of the LIBS library information, calculates a probability that the spectral data will belong to each of the multiple clusters using first regress component analysis using first training data for the spectral data, performs second regression component analysis using second training data which belongs to each cluster with respect to the spectral data, and discriminates the type of metal sample using the calculated probability and the second regression component analysis result.

In the exemplary embodiment, the first regression component analysis may be full-scale regression component analysis for the metal sample.

In the exemplary embodiment, the signal processing device may estimate an element concentration which is a final regression component analysis result by a weighted sum of the calculated probability and the second regression component analysis result and discriminate the type of metal sample using the LIBS database and the estimated element concentration.

According to an exemplary embodiment of the present invention, a metal sorting system and an operating method thereof can sort metal more precisely by using a correlation of metal component distributions of an LUIS library database.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The accompanying drawings, which are to provide a further understanding of the exemplary embodiment, provide the exemplary embodiments together with the detailed description. It is to be understood, however, that technical features of the exemplary embodiment are not limited to specific drawings and features disclosed in the respective drawings may be combined with each other to constitute a new exemplary embodiment.

FIG. 1 is a block diagram exemplarily illustrating a metal sorting system 100 according to an exemplary embodiment of the present invention.

FIG. 2 is a diagram exemplarily illustrating a metal sorting process of the metal sorting system 100 illustrated in FIG. 1.

FIG. 3 is a diagram exemplarily illustrating a distribution of metal alloys for a correlation of Cu—Zn and Fc—(Cr+Ni).

FIG. 4 is a diagram exemplarily illustrating a correlation of Cu—Zn and Cu—Ni element concentrations.

FIG. 5 is a diagram exemplarily illustrating a multi-cluster setting process according to an exemplary embodiment of the present invention.

FIG. 6 is a diagram illustrating a ternary diagram according to an exemplary embodiment of the present invention.

FIG. 7 is a flowchart exemplarily illustrating a metal sorting process 120 according to an exemplary embodiment of the present invention.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

The contents of the present invention will be clearly and specifically disclosed so that those skilled in the art can easily carry out the present invention with reference to the following drawings.

The present invention may have various modifications and various embodiments and specific embodiments will be illustrated in the drawings and described in detail in the specification. However, this does not limit the present invention to specific exemplary embodiments, and it should be understood that the present invention covers all the modifications, equivalents and replacements included within the idea and technical scope of the present invention. Terms including as first, second, and the like are used for describing various constituent elements, but the constituent elements are not limited by the terms.

The terms are used to discriminate one constituent element from another component. For example, a first component may be referred to as a second component, and similarly, the second component may be referred to as the first component without departing from the scope of the present invention. It should be understood that, when it is described that a component is "connected to" or "accesses" another component, the component may be directly connected to or access the other component or a third component may be present therebetween. In contrast, it should be understood that, when it is described that an element is "directly connected to" or "directly access" another element, it is understood that no element is present between the element and another element.

Meanwhile, other expressions describing the relationship of the components, that is, expressions such as "between" and "directly between" or "adjacent to" and "directly adjacent to" should be similarly interpreted. Terms used in the present application are used only to describe specific exemplary embodiments, and are not intended to limit the present invention. A singular form may include a plural form if there is no clearly opposite meaning in the context.

In the present application, it should be understood that term "include" or "have" indicates that a feature, a number, a step, an operation, a component, a part or the combination thereof described in the specification is present, but does not exclude a possibility of presence or addition of one or more other features, numbers, steps, operations, components, parts or combinations thereof in advance. If it is not contrarily defined, all terms used herein including technological or scientific terms have the same meanings as those generally understood by a person with ordinary skill in the art. Terms which are defined in a generally used dictionary should be interpreted to have the same meaning as the meaning in the context of the related art, and are not interpreted as an ideal meaning or excessively formal meanings unless clearly defined in the present application.

A metal sorting system and an operating method thereof according to exemplary embodiments of the present invention determine component distributions of metals through prior information and perform multiple clustering according to correlation characteristics of the component distributions and analyze a regress component trained based on each cluster, thereby enabling concentration analysis and metal type sorting with higher accuracy.

FIG. 1 is a block diagram exemplarily illustrating a metal sorting system 100 according to an exemplary embodiment of the present invention. Referring to FIG. 1, the metal sorting system 100 may include an LIBS device 110, a signal processor 120, an LIBS library database 130, and a discharge device 140. Although not illustrated, a transfer apparatus may be implemented to transfer metals. In the exemplary embodiment, the transfer apparatus may include a conveyor belt. A sensing device may be implemented to sense a location, a shape, and a color of the metal on the belt.

The LIBS device 110 may be implemented to irradiate the transferred metal with an LIBS laser to output spectral data related to each metal component. The LIBS device 110 may be implemented by a focus control driving technique (autofocus) and a scanning driving technique (Galvano). The focus control driving technique uses a principle in which a focal distance reaching a sample surface is finally varied by varying an interval between two lenses rapidly. The scanning driving technique uses a principle in which a mirror performing two rotation motions performs a high-speed rotation motion to change a laser irradiation direction. Additionally, the LIBS device 110 may apply a surface decontamination driving technique. The surface decontamination driving technique may include a self-cleaning optimal condition and process technique that removes contaminants of a heavily contaminated surface through high-power laser ablation and then, measures an LIBS signal.

The signal processing device 120 may be implemented to sort the type of sample metal using spectrum data and the LIBS library information transmitted from the LIBS device 110.

The LIBS library database 130 may be implemented to store the LIBS library information. The LIBS library information may include information on the correlation between various parameters including a temperature, humidity, fine dust concentration, experimental variables, existing measured data, and the like and metal element components.

The discharge device 140 may be implemented to discharge the metals to another collection box for each type. For example, the discharge device 140 may include an air knife, a kicker, and the like. In the exemplary embodiment, the metal may include copper, aluminum, stainless steel, and the like.

The metal sorting system 100 according to the exemplary embodiment of the present invention performs multiple clustering by using the correlation of the metal component distribution of the LIBS library database 130 and then, performs regression component analysis for each cluster, thereby more precisely sorting the metals.

FIG. 2 is a diagram exemplarily illustrating a metal sorting process of the metal sorting system 100 illustrated in FIG. 1.

Component distribution features of various metals may be analyzed by using the prior information including the temperature, the humidity, a fine dust concentration, the experimental variables, the existing measured data, and the like of the LIBS library database 130. Thereafter, multiple clustering according to a metal component feature may be performed. First regression component analysis may be performed, which uses all training sets with respect to new spectral data, that is, a normalized signal and a cluster for a sample metal may be probabilistically determined among predetermined multiple clusters. Second regression component analysis may be performed, which uses the training set of the determined cluster. Finally, the metal type for the metal sample may be sorted according to the weighted sum result of the second regression component analysis and the probabilities.

Hereinafter, the setting of multiple clusters according to the metal component distribution will be described. By using the prior information in databases provided by the National Institute of Standards and Technology (NIST) and Brammerstandard, the metal component distribution may be analyzed to determine what correlations are exhibited by an elemental composition of various metals. For example, there are few metals containing only 20 to 40% of copper elements. Further, in case of stainless steel, the concentration of iron shows an inverse linear correlation with the sum of concentrations of chromium and nickel.

FIG. 3 is a diagram exemplarily illustrating a component distribution of metal alloys for a correlation of Cu—Zn and Fe—(Cr+Ni). As illustrated in a upper graph of FIG. 3, the correlation of Cu and Zn may be classified into a cluster showing in which Cu and Zn have a 1-x correlation, a cluster in which Cu shows a concentration of 70 to 90% and Zn shows a concentration of 10% or less, and a cluster in which both Cu and Zn concentrations are smaller than 10%. As such, the multiple clusters may be set according to the correlation for the component distribution of the metals. As illustrated in a bottom graph of FIG. 3, the correlation of Fe—(Cr+Ni) shows that there may be cases in which all three components contain a trace amount. In most other metal alloys, the correlation between Fe and (Cr+Ni) concentrations shows a linear relationship.

FIG. 4 is a diagram exemplarily illustrating a correlation of Cu—Zn and Cu—Ni element concentrations. Looking at data of the copper alloy, there are a total of 1835 copper alloys contained in the database. Among them, there are 1067 alloys in which Cu and Zn concentrations have a complementary relationship, and there are 206 alloys in which Cu, and Ni and Zn concentrations have the complementary relationship, and there are 98 alloys in which Cu, and Al and Zn concentrations have the complementary relationship. As such, there is a linear correlation of major element distributions in any metal.

In the case of the most important element component in the metal spectrum, information of a main element component may cause an inaccurate analysis result because of physical phenomena such as self absorption, etc. Therefore, information of a main element component next to the main element component is very important. Therefore, it is efficient to set multiple clusters according to the elements having the linear relationship with the main component. Analyzing an element concentration correlation for setting the multiple clusters is required.

FIG. 5 is a diagram exemplarily illustrating a multi-cluster setting process according to an exemplary embodiment of the present invention. As illustrated in FIG. 5, the clusters may be classified by considering the main component first, clusters may be classified by taking into account the relationship between the components showing a highest concentration (first concentration) next to the main component concentration and a main component, and clusters may be classified in an order considering a component showing a high concentration (second concentration) next to the first concentration. As described above, information on the element showing the second concentration is very important. Accordingly, clustering considering the correlation of the element is very important for the second concentration.

FIG. 6 is a diagram illustrating a ternary diagram according to an exemplary embodiment of the present invention. Multiple clusters set based on the above criteria may be expressed in the ternary diagram. Multidimensional graphs are intuitively difficult to express to be seen by our eyes. For this reason, it is possible to confirm how the distribution is clustered for the three concentrations even in a two-dimensional space and whether the actually set cluster is clearly visible through the ternary diagram.

As described above, in FIGS. 3 to 6, the setting of multiple clusters according to the distribution of the metal components has been described using the prior information. Under the set multiple clusters, a metal type sorting operation for an unknown metal sample will begin.

The first regression component analysis for an unknown sample will be preferentially performed. That is, full-scale regression component analysis for the unknown sample will be performed. In the first regression component analysis, all training data ($Y_{all}$, $X_{all}$) provided before distinguishing the cluster are set to a training set and training-analyzed to obtain parameters ($\tilde{B}$, $\tilde{B}_0$) for regression component analysis.

$$Y_{all}, X_{all} \rightarrow \tilde{B}_{all}, \tilde{B}_{all,0}$$

Here, $X_{all}$ represents spectral data of all metals, $Y_{all}$ represents the element concentration, $\tilde{B}$ represents a coefficient of regression, and $\tilde{B}_0$ represents a bias of regression.

When all spectral data for unknown i metal data $X_i$ are set to the training set, a regression component analysis result $\hat{Y}_i$ may be calculated as below.

$$\hat{Y}_i = X_i \tilde{B}_{all} + \tilde{B}_{all,0}$$

Here, $X_i$ represents spectral data of unknown i metal and $\hat{Y}_i$ represents an estimated element concentration.

As described above, once the first regression component analysis is completed, the probability of each cluster according to the first regression component analysis result may be calculated. That is, a probabilistic discrimination may be performed with respect to which cluster among predetermined multiple clusters a component of the unknown sample belongs to. A probability $p(\theta_n|\hat{Y}_i)$ that the spectral data for the sample will belong to each cluster may be calculated through the first regression component analysis, that is, the full-scale regression component analysis result $\hat{Y}_i$.

When a variable of cluster n is $\theta_n$, a probability $$p(\hat{Y}_i|\theta_n) = \int\int \left[ \frac{1}{\sqrt{(2\pi)^k C_n}} e^{\left(-\frac{1}{2}(\hat{Y}_i-\mu_n)^T C_n^{-1}(\hat{Y}_i-\mu_n)\right)} \right] dV$$

that if the spectral data belongs to cluster n, the full-scale regression component analysis result will become $\hat{Y}_i$ and a probability $$p(\theta_n) = \frac{\text{number of metal scraps which belong to cluster } n}{\text{total number of metal scraps}}$$

that the cluster will become n is a probability $p(\hat{Y}_i)$ that the regression component analysis result will become $\hat{Y}_i$.

In the exemplary embodiment, a probability $p(\theta_n|\hat{Y}_i)$ that the first regression component analysis result will belong to each cluster may be calculated by using the Bayesian rule.

$$p(\theta_n|\hat{Y}_i) = \frac{p(\hat{Y}_i|\theta_n)p(\theta_n)}{p(\hat{Y}_i)}$$

$$p(\theta_1|\hat{Y}_i) + p(\theta_2|\hat{Y}_i) + p(\theta_3|\hat{Y}_i) + \ldots + p(\theta_n|\hat{Y}_i) = 1$$

Once the probability for each cluster is calculated as described above, the second regression component analysis will be performed, which performs training with each cluster data. Here, the cluster data means training data which belongs to each cluster.

The training and test are performed by each cluster data, and as a result, a final regression component analysis result of a weighted sum of the probability and the second regression analysis is shown in a table below.

TABLE 1

|  | Class 1 | Class 2 | Class 3 | ... | Class N |
|---|---|---|---|---|---|
| Probability | $p(\theta_1|\hat{Y}_i)$ | $p(\theta_2|\hat{Y}_i)$ | $p(\theta_3|\hat{Y}_i)$ | ... | $p(\theta_N|\hat{Y}_i)$ |
| Regression analysis result | $\hat{y}_{i1}$ | $\hat{y}_{i2}$ | $\hat{y}_{i3}$ | ... | $\hat{y}_{iN}$ |

$$\widehat{Y\_w}_i = p(\theta_1|\hat{Y}_i)\hat{y}_{i1} + p(\theta_2|\hat{Y}_i)\hat{y}_{i2} + p(\theta_3|\hat{Y}_i)\hat{y}_{i3} + \ldots + p(\theta_N|\hat{Y}_i)\hat{y}_{iN}$$

Here, $\widehat{Y\_w}_i$ represents a final regress analysis result value weighted for unknown i metal, $p(\theta_N|\hat{Y}_i)$ represents a probability that unknown x metal will belong to Class N, and $\hat{y}_{i1}$ represents a second regress component analysis result value in Class N for unknown a metal.

Meanwhile, by the weighted sum of the probability $p_{i1} \ldots p_{iN}$ calculated through the first regression component analysis and the second regression component analysis result $\hat{y}_{i1} \ldots \hat{y}_{iN}$ in each cluster, an estimated concentration $\widehat{Y\_w}_i$ may be calculated as the final regression component analysis result for discriminating the metal type.

As described above, after the second regression component analysis is performed, the metal type for the sample through multi-cluster based regression component analysis may be discriminated. That is, the metal type of an unknown sample may be discriminated through the multi-cluster-based regression component analysis. Through an estimated concentration value $\widehat{Y\_w}_i$ finally calculated, which metal type the corresponding metal is by using the existing database. As described above, the process may be applied to a metal sorting algorithm.

FIG. 7 is a flowchart exemplarily illustrating a metal sorting process according to an exemplary embodiment of the present invention. Referring to FIGS. 1 to 7, an operation of the metal sorting system 100 may be performed as follows.

Component distribution analysis for various metals may be performed using the LIBS library information (S110). Multiple clusters may be preset in accordance with the metal distribution (S120). Here, steps S110 and S120 are preliminary tasks for performing multiple cluster regression analysis. A first regression component analysis using all training data may be performed with respect to the spectral data for the metal sample received from the LIBS device 110 (S130). Here, the first regression component analysis may be a full-scale regression component analysis using first training data (all training sets). According to the first regression component analysis result, the probability that the metal sample will belong to each cluster may be calculated (S140). The second regression component analysis using second training data which belongs to each cluster may be performed (S150). Then, a final metal concentration for at least one metal may be estimated by the weighted sum of the calculated probability and the second regression component analysis result (S160) and the metal type for the metal sample may be discriminated based on the estimated metal concentration (S170).

The steps and/or operations according to the present invention may occur in different orders, in parallel, or concurrently in other exemplary embodiments for other epochs or the like, as may be understood by those skilled in the art.

Depending on the exemplary embodiment, at least some or all of the steps and/or operations may be implemented or preformed by using commands, programs, and interactive data structures server stored in one or more non-transitory computer-readable media, and one or more processors driving a client and/or a server. The one or more non-transitory computer-readable media may be, by way of example, software, firmware, hardware, and/or any combination thereof. Further, the functions of the "module" discussed in this specification may be implemented by software, firmware, hardware, and/or any combination thereof.

One or more non-transitory computer-readable media and/or means for implementing/performing one or more operations/steps/modules of exemplary embodiments of the present invention may be implemented as application-specific integrated circuits (ASICs), standard integrated circuits, controllers and/or embedded controllers performing appropriate commands, which include a microcontroller, field-programmable gate arrays (FPGAs), complex programmable logic devices (CPLDs), and devices equivalent thereto, but are not limited thereto.

Prior clustering-based regression component analysis for soft sorting of metal scrap may be performed in the laser induced breakdown spectroscopy according to the exemplary embodiment of the present invention.

A pre-clustering-based regression component technique may be performed for identifying the scrap metal using the laser induced breakdown spectroscopy (LIBS) according to the exemplary embodiment of the present invention. Estimation accuracy, especially a line strongly correlated with an object may be enhanced by using spectral lines of some of other elements in order to estimate the concentration of a basic metal element from an LIBS spectrum. Depending on a correlation pattern, alloys of the same base metal are divided into several clusters based on previous information, and regression models of different clusters may be used together with corresponding weights.

For evaluation, prior information may be used for clustering and pre-determination in the NIST/Brammer data set. The prior information includes appropriately 10,000 aluminum, copper, and steel alloy samples. Heterogeneous metal alloys may be sorted into different clusters according to the prior determination and then, the same basic metal alloy may be clustered based on a relationship with a secondary or next element.

Basic element regression component analysis may be individually modeled for utilization of the relationship in order to estimate the corresponding concentration. For example, clusters of copper alloys may be classified into four groups based on the relationship of Cu—Zn, Cu—Al, Cu—Ni and Cu—Pb+Sn in the data set. Among them, the Cu alloy showing the Cu—Zn relationship may contain Zn having a Cu concentration of approximately 100-Zn concentration and a Zn peak may be advantageous in estimating the Cu concentration. Thus, once a test sample is known as a Cu—Zn replenishment cluster, the Cu concentration may be better predicted using an extra Zn peak.

PLS regression component analysis may then be used for quantitative analysis. Quantitative analysis of samples unknown with PLS may be performed using all data sets for the predetermination. The estimated result provides a cluster to which the unknown sample belongs and quantitative analysis with the PLS may be performed again with the data set of separated clusters. However, if the samples are incorrectly clustered with a noise effect, the selected regression model may have poor predictive performance.

In order to mitigate a problem of a decision making error, the present invention proposes soft decision based clustering and synthesizes the final regression result as a weighted sum of regression models of other clusters. RMSE of nonclustered regression is 1.4350%, while the RMSE of clustering-based regression shows better performance as 1.0835% using a root-mean-square-error (RMSE) method, compared with the regression result of Cu—Zn alloy. In this result, a numerical simulation shows a validity of the proposed invention.

Meanwhile, the above-described contents of the present invention are only specific exemplary embodiments for carrying out the invention. The present invention will include not only concrete and practical means themselves, but also technical ideas which are abstract and conceptual ideas that can be utilized as future technologies.

As described above, the exemplary embodiments have been described and illustrated in the drawings and the specification. The exemplary embodiments were chosen and described in order to explain certain principles of the invention and their practical application, to thereby enable others skilled in the art to make and utilize various exemplary embodiments of the present invention, as well as various alternatives and modifications thereof. As is evident from the foregoing description, certain aspects of the present invention are not limited by the particular details of the examples illustrated herein, and it is therefore contemplated that other modifications and applications, or equivalents thereof, will occur to those skilled in the art. Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

What is claimed is:

1. An operating method of a metal sorting system using laser induced breakdown spectroscopy (LIBS), wherein the metal sorting system comprises a signal processing device, the method comprising:
    analyzing, by the signal processing device, a metal component distribution for various metals using LIBS library information;
    setting, by the signal processing device, multiple clusters according to the metal component distribution;
    performing, by the signal processing device, first regression component analysis using first training data with respect to spectral data of a metal sample;

calculating, by the signal processing device, a probability that the spectral data will belong to each of the set multiple clusters using the first regress component analysis result;

performing, by the signal processing device, second regression component analysis using second training data which belongs to each cluster with respect to the spectral data of the metal sample; and discriminating, by the signal processing device, a type of metal sample by a weighted sum of the calculated probability and the second regression component analysis result, wherein the metal sorting system further comprises a LIBS device outputting the spectral data of the metal sample by irradiating the metal sample with a laser, and a discharge device discharging metals to different collection boxes according to the discriminated metal type.

2. The method of claim 1, wherein the LIB S library information includes prior information including at least one of a temperature, humidity, fine dust concentration, experimental variables, and existing measured data.

3. The method of claim 1, wherein the metal component distribution includes information on a correlation between the LIBS library information and the metal.

4. The method of claim 1, wherein the setting of the multiple clusters includes
classifying the clusters by considering a main component, and
classifying the clusters by considering a linear relationship between a component having a first concentration and the main component, and
the first concentration is lower than a concentration of the main component.

5. The method of claim 4, wherein the setting of the multiple clusters further includes classifying the clusters by considering the linear relationship between a component having the second concentration and the main component, and
the second concentration is lower than the first concentration.

6. The method of claim 1, wherein the calculating of the probability further includes performing soft sorting for the metal sample according to the calculated probability.

7. The method of claim 1, wherein the calculating of the probability includes calculating a probability that the spectral data will belong to each cluster using a Bayesian rule.

8. The method of claim 1, wherein the performing of the first regression component analysis includes estimating an element concentration of unknown metal data by training the spectral data using the first training data, and
the first training data is all training data.

9. The method of claim 8, wherein the performing of the second regression component analysis includes estimating the element concentration of the unknown metal data by training the spectral data using the second training data.

10. The method of claim 9, wherein the discriminating the type of metal sample includes
calculating a final regression analysis result by the weighted sum of the second regression component analysis result and the calculated probability,
estimating at least one metal concentration value depending on the final regression analysis result, and
discriminating the type of metal sample using the LIBS library information and the estimated concentration value.

11. A metal sorting system using laser induced breakdown spectroscopy (LIBS), the system comprising:
an LIBS device outputting spectral data of a metal sample by irradiating the metal sample with a laser;
a signal processing device discriminating a type of metal sample using the spectral data and LIBS library information; and
a discharge device discharging metals to different collection boxes according to the discriminated metal type,
wherein the signal processing device sets multiple clusters according to the LIBS library information and a metal component distribution, calculates a probability that the spectral data will belong to each of the multiple clusters using first regress component analysis using first training data for the spectral data, performs second regression component analysis using second training data which belongs to each cluster with respect to the spectral data, and discriminates the type of metal sample using the calculated probability and the second regression component analysis result.

12. The system of claim 11, wherein the first regression component analysis is full-scale regression component analysis for the metal sample.

13. The system of claim 12, wherein the signal processing device estimates an element concentration which is a final regression component analysis result by a weighted sum of the calculated probability and the second regression component analysis result and discriminates the type of metal sample using the LIBS database and the estimated element concentration.

* * * * *